(12) United States Patent
Plückthun et al.

(10) Patent No.: US 6,589,741 B2
(45) Date of Patent: *Jul. 8, 2003

(54) POLYSOME DISPLAY IN THE ABSENCE OF FUNCTIONAL SSRA-RNA

(75) Inventors: Andreas Plückthun, Zurich (CH); Jozef Hanes, Schenefeld (DE); Lutz Jermutus, Gummersbach (DE)

(73) Assignee: University of Zurich, Zurich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/953,321

(22) Filed: Sep. 14, 2001

(65) Prior Publication Data

US 2002/0115083 A1 Aug. 22, 2002

Related U.S. Application Data

(63) Continuation of application No. 09/425,585, filed on Oct. 22, 1999, now Pat. No. 6,348,315, which is a continuation of application No. PCT/EP98/02420, filed on Apr. 23, 1998.

(30) Foreign Application Priority Data

Apr. 23, 1997 (EP) ............................................. 97106753

(51) Int. Cl.[7] ............................ C12Q 1/68; C12Q 1/00; C07H 21/02; C07H 21/04; C12N 15/00
(52) U.S. Cl. ............................... 435/6; 435/4; 435/69.1; 435/69.7; 436/501; 436/518; 436/536; 536/23.1; 536/23.4; 536/24.5
(58) Field of Search ............................... 435/4, 6, 69.1, 435/69.7; 436/501, 518, 536; 536/23.1, 23.4, 24.1, 24.5

(56) References Cited

U.S. PATENT DOCUMENTS

| | | | | |
|---|---|---|---|---|
| 5,466,580 A | * | 11/1995 | White et al. | 435/7.1 |
| 5,658,754 A | * | 8/1997 | Kawasaki | 435/69.1 |
| 5,922,545 A | * | 7/1999 | Mattheakis et al. | 435/6 |
| 6,348,315 B1 | * | 2/2002 | Pluckthun et al. | 435/6 |

FOREIGN PATENT DOCUMENTS

| | | |
|---|---|---|
| WO | WO 91/05058 | 4/1991 |
| WO | WO 93/03172 A1 | 2/1993 |
| WO | WO 95/11922 | 5/1995 |

OTHER PUBLICATIONS

Hanes, J. and Plückthun, A., "In vitro selection and evolution of functional proteins by using ribosome display", Proc. Natl. Acad. Sci. 94: 4937–4942 (1997).

Hirao, I. et al., "Stabilization of mRNA in an *Escherichia coli* cell–free translation system", FEBS 321: 196–172 (1993).

Keiler, K. et al., "Role of a peptide tagging system in degradation of proteins synthesized from damaged messenger RNA", Science 271: 990–993 (1996).

Ryabova, L. et al., "Functional antibody production using cell0free translation: Effects of protein disulfide isomerase and chaperones", Nature Biotechnology 15: 79–84 (1997).

Irvine, D. et al., "Systematic Evolution of Ligands by Exponential Enrichment with Integrated Optimization by Non–linear Analysis", J. Biol., 222, 739–761 (1991).

Mattheakis, L.C. et al., "An invitro Polysome Display System to Identifying Ligands from Very Large Peptide Libraries", Proc. Natl. Acad. Sci. USA, 91, 9022–9026 (1994).

Komine, Y. et al., "A tRNA–like Structure is Present in 10Sa RNA, a Small Stable RNA from *Escherichia coli*", Proc. Natl. Acad. Sci. USA, 91, 9223–9227 (1994).

Tu, G. et al., "C–terminal Extension of Truncated Recombinant Proteins in *Escherichia coli* with a 10Sa RNA Decapeptide", The Journal of Biological Chemistry, 270, 9322–9326 (1995).

Retallack, D.M. et al., "A Role for a Small Stable RNA in Modulating the Activity of DNA–Binding Proteins", Cell 83, 227–235 (1995).

Roche, E.D. et al., "SsrA–mediated Peptide Tagging Caused by Rare Condons and tRNA Scarcity", The EMBO Journal, 18, 4579–4589 (1999).

Newbury et al., Cell 48:297–310, Jan. 1987.

The 1985 Bethesda Research Laboratories catalog, p. 21., BRL, Gaithersburg, MD.

Berger et al., Biochemistry (18) 23: 5143–5149, 1979.

\* cited by examiner

*Primary Examiner*—David Guzo
*Assistant Examiner*—Gerald G. Leffers, Jr.
(74) *Attorney, Agent, or Firm*—Heller Ehrman White and McAuliffe (57) ABSTRACT

The present invention relates to methods for identifying nucleic acid molecules encoding (poly)peptides that interact with target molecules. The method of the present invention is particularly characterized by an in vitro translation step under conditions that allow formation of polysomes in the presence of antisense oligonucleotides complementary to the tag-coding sequence of ssrA-RNA. The present invention further relates to kits that are useful for carrying out the method of the invention.

9 Claims, 5 Drawing Sheets

SEQUENCE LISTING

<160> NUMBER OF SEQ ID NOS: 15

<210> SEQ ID NO 1
<211> LENGTH: 11
<212> TYPE: PRT
<213> ORGANISM: Escherichia coli

<400> SEQUENCE: 1

Ala Ala Asn Asp Glu Asn Tyr Ala Leu Ala Ala
 1               5                  10

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide ON10

<400> SEQUENCE: 2
ttaagctgct aaagcgtagt tttcgtcgtt tgcgacta                    38

<210> SEQ ID NO 3
<211> LENGTH: 80
<212> TYPE: DNA
<213> ORGANISM: Artificial Sequence
<220> FEATURE:
<223> OTHER INFORMATION: Description of Artificial Sequence:
      Oligonucleotide ON1

<400> SEQUENCE: 3
tttcccgaat tgtgagcgga taacaataga aataattttg tttaacttta agaaggagat    60
atatccatgg actacaaaga                                               80

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide ON2

<400> SEQUENCE: 4
tttaagcagc tcgatagcag cac                                   23

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence:
      Oligonucleotide ON3

<400> SEQUENCE: 5
atatatgtcg acgaaattaa tacgactcac tatagggaga ccacaacggt ttcccgaatt    60
gtg                                                                 63

```
<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide ON4

<400> SEQUENCE: 6
agacccgttt agaggcccca agggttatg gaattcacct ttaagcagct c              51

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide ON5

<400> SEQUENCE: 7
tcagtagcga cagaatcaag                                                20

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence:
      Oligonucleotide ON6

<400> SEQUENCE: 8
gaaattaata cgactcacta tagggttaac tttagaagga ggtatatcca tggactacaa    60
aga                                                                  63

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide ON7

<400> SEQUENCE: 9
ggcccacccg tgaaggtgag cctcagtagc gacag                               35

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide ON8

<400> SEQUENCE: 10
tttaagcagc tcatcaaaat cacc                                           24

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide ON9

<400> SEQUENCE: 11
acatggtaac ttttttcacca gcggtaacgg                                    30
```

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Peptide
      Linker

<400> SEQUENCE: 12

Gly Gly Gly Gly Ser Gly Gly Gly Gly Ser Gly Gly Gly Gly Ser Gly
 1               5                  10                  15

Gly Gly Gly Ser
            20

<210> SEQ ID NO 13
<211> LENGTH: 33
<212> TYPE: PRT
<213> ORGANISM: Unknown Organism
<220> FEATURE:
<223> OTHER INFORMATION: Description of Unknown Organism: Modified GCN4
      (7P14P) peptide sequence from Saccharomyces cerevisiae

<400> SEQUENCE: 13

Arg Met Lys Gln Leu Glu Pro Lys Val Glu Glu Leu Leu Pro Lys Asn
 1               5                  10                  15

Tyr His Leu Glu Asn Glu Val Ala Arg Leu Lys Lys Leu Val Gly Glu
            20                  25                  30

Arg

<210> SEQ ID NO 14
<211> LENGTH: 74
<212> TYPE: DNA
<213> ORGANISM: Artificial Sequence
<220> FEATURE:
<223> OTHER INFORMATION: Description of Artificial Sequence:
      Oligonucleotide SDA

<400> SEQUENCE: 14
agaccacaac ggtttccctc tagaaataat tttgtttaac tttaagaagg agatatatcc      60
atggactaca aaga                                                       74

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide T7B

<400> SEQUENCE: 15
atacgaaatt aatacgactc actataggga gaccacaacg g                         41

POLYSOME DISPLAY IN THE ABSENCE OF FUNCTIONAL SSRA-RNA

This application is a continuation of U.S. patent application Ser. No. 09/425,585, now U.S. Pat. No. 6,348,315, filed Oct. 22, 1999, which is a continuation of International Application PCT /EP98/02420, filed Apr. 23, 1998, which designates the United States.

BACKGROUND OF THE INVENTION

The present invention relates to methods for identifying nucleic acid molecules encoding (poly)peptides that interact with target molecules. The method of the present invention is particularly characterized by an in vitro translation step under conditions that allow formation of polysomes in the presence of antisense oligonucleotides complementary to the tag-coding sequence of ssrA-RNA. The present invention further relates to kits that are useful for carrying out the method of the invention.

Evolutionary methods may bring the refinement to protein engineering which is beyond the powers and accuracy of rational design today. Evolution can be defined as a succession of "generations", cycles of genetic diversification, followed by Darwinian selection for a desired phenotypic property. In classic experiments, nucleic acids have been evolved for physical properties (Saffhill,. R., Schneider-Bernloehr, H., Orgel, L. E. & Spiegelman, S. (1970) *J. Mol. Biol.* 51, 531–539) in vitro, and in this case, the substance conferring the phenotype was identical to the genetic material. Oligonucleotide ligands, usually single stranded RNA, have been identified for many targets by SELEX (Gold, L., Polisky, B., Uhlenbeck, O. & Yarus, M. (1995) *Annu. Rev. Biochem.* 64, 763–797; Irvine, D., Tuerk, C. & Gold, L. (1991) *J. Mol. Biol.* 222, 739–761), in which a synthetic DNA library is transcribed, the RNA selected for binding, reverse transcribed and amplified over several rounds. Early experiments with proteins as the carrier of the phenotype, clearly of much broader applicability, had relied on living cells for effecting the coupling between gene and protein, either directly or via the production of phages or viruses (Phizicky, E. M. & Fields, S. (1995) *Microbiol. Rev.* 59, 94–123). Since in this type of experiment the DNA library as the information carrier for encoded protein diversity has to be transformed or transfected into bacterial or eukaryotic cells, the available diversity was severely limited by the low efficiency of DNA uptake (Dower, W. J. & Cwirla, S. E. (1992) in *Guide to Electroporation and Electrofusion*, eds. Chang, D. C., Chassy, B. M., Saunders, J. A. & Sowers, A. E. (Academic Press, San Diego), pp. 291–301). Furthermore, in each generation, the DNA library had to be first ligated into a replicable genetic package by which diversity was again decreased. In addition, many promising variants would have to be selected against in the host environment. Only very few studies (Yang, W. P., Green, K., Pinz-Sweeney, S., Briones, A. T., Burton, D. R. & Barbas 3rd., C. F. (1995) *J. Mol. Biol.* 254, 392–403) have carried protein optimization through more than one generation using methods such as phage display, since this requires repeated switching between in vitro diversification and in vivo screening—a laborious process.

With the goal of circumventing or improving this process, a number of laboratories have designed novel systems that are based on the immediate vicinity and physical connection of mRNA and corresponding (poly)peptides during translation. Thus, a series of studies have shown that specific mRNAs can be enriched by immunoprecipitation of polysomes (Schechter, I. (1973) *Proc. Natl. Acad. Sci. U.S.A.* 70, 2256–2260; Payvar, F. & Schimke, R. T. (1979) *Eur. J. Biochem.* 101, 271–282; Kraus, J. P. & Rosenberg, L. E. (1982) *Proc. Natl. Acad. Sci. U.S.A.* 79, 4015–4019). Recently, Mattheakis and coworkers reported an affinity selection of a short peptide from a library using polysomes, in order to connect genotype and phenotype in vitro (Mattheakis, L. C., Bhatt, R. R. & Dower, W. J. (1994) *Proc. Natl. Acad. Sci. U.S.A.* 91, 9022–9026; WO95/11922).

This system employs an in vitro translation system that is preferentially coupled to an in vitro transcription system. The translation system allows the simultaneous isolation of mRNA and (poly)peptide in a polysome complex after a suitable screening step for the (poly)peptide. Preferably, the (poly)peptides in Mattheakis' system are comprised of two components, one of which is the peptide to be screened and the second is a tether segment that binds to the mRNA. Co-isolation of mRNA and (poly)peptide in the polysome complex can possibly be improved with the help of a translation stalling sequence even though the existence of such sequences is still unclear for *E. coli*. This sequence possibly enhances the overall stability of the polysome complex by decreasing the translation rate and thus allows for suitable conditions for the concomitant screening and isolation of (poly)peptide and corresponding mRNA.

Similar work has earlier been reported by Gold and colleagues (WO 93/03172) and Kawasaki and co-workers (WO 91/05058). Although the above-described systems have established a means of characterizing a nucleic acid via the identification of a protein encoded by said nucleic acid, there are practical limitations with respect to the efficiency of the ribosome displays of the nascent (poly)peptide. The technical problem underlying the present invention was therefore to increase the efficiency of (i) synthesis of a collection of stable RNA molecules and (ii) translation of said RNA molecules, and thereby to achieve an increased efficiency of the use of polysomes in screening. The solution to said technical problem is achieved by providing the embodiments characterized in the claims.

SUMMARY OF INVENTION

Accordingly, the present invention relates to a method for identifying a nucleic acid molecule encoding a (poly)peptide that interacts with a target molecule comprising the following steps:

(a) translating a population of mRNA molecules devoid of stop codons in the correct reading frame in an in vitro translation system, said translation system either comprising antisense oligonucleotides complementary to the tag-coding sequence of ssrA-RNA or being free of ssrA-RNA, under conditions that allow the formation of polysomes;

(b) bringing the polysomes so formed into contact with said target molecules under conditions that allow the interaction of the (poly)peptides encoded by said mRNA molecules and displayed by said polysomes with said target molecules;

(c) separating polysomes displaying (poly)peptides that interact with said target molecules from polysomes displaying no such (poly)peptides; and (d) identifying the nucleic acid molecule encoding a (poly)peptide displayed in a polysome that interacts with said target molecules.

The term "(poly)peptide" as used in the present invention relates both to peptides as well as to polypeptides. Said (poly)peptides may either comprise a natural or a recombinantly engineered amino acid sequence. The latter alternative also includes fusion proteins.

According to the present invention, the term "polysome" refers to a complex formed by at least one, preferably several ribosomes and mRNA during translation.

The population of mRNA molecules may be of varying origin. For example, it may be derived from a cDNA library. In an alternative embodiment, it may be directly derived from cells or tissue. Particularly advantageous is also the use of the present invention in mutagenized (poly)peptides to find improved variants. Alternatively, synthetic protein or peptide libraries or antibody libraries can be used.

The term "tag-coding sequence of ssrA-RNA" relates to a nucleic acid sequence encoding the amino acid sequence AANDENYALAA (SEQ ID NO: 1). This sequence has been described in Keiler et al., Science 221 (1996), 1990–1993.

The antisense oligonucleotides comprised in the translation system employed in the method of the invention are of a suitable length to hybridize to the tag-coding sequence of ssrA-RNA and block translation thereof under conditions that allow the formation of polysomes.

A translation system being free of ssrA-RNA can, for example, be derived from E. coli strains lacking a functional ssrA gene such as X90 ssrA1::cat (Keiler et al., Science 221 (1996), 1990–1993), N2211 or NM101 (Tu et al., J. Biol. Chem. 270 (1995), 9322–9326), W3110 ΔssrA (Komine et al., Proc. Natl. Acad. Sci. U.S.A. 91 (1994), 9223–9227), K7823 or K6676 (Retallack and Friedman, Cell 83 (1995), 227–235).

Conditions that allow the interaction of the (poly)peptides encoded by the translated mRNA molecules and displayed by said polysomes with corresponding target molecules can, without undue burden, be established by the person skilled in the art. Such conditions are, for example, derivable from the teachings of WO 95/11922, WO 93/03172 and WO 91/05058 or from the appended examples. As is well known in the art, said conditions also rely on the screening procedure that is employed for detecting said interactions.

The separation of the polysomes that display (poly) peptides which interact with the target molecules from polysomes displaying no such (poly)peptides can be effected according to known procedures. Again, the separation technique employed may well depend on the screening system that is used. A convenient method of separating the aforementioned polysomes is, for example, based on affinity chromatography wherein the target molecules are bound to the column material.

The identification of the nucleic acid molecule encoding the selected (poly)peptide can be achieved by any suitable means and is most conveniently achieved by sequencing the nucleic acid molecule, for example, by sequencing the mRNA or the DNA, after cloning into a vector. For identification of the mRNA, it may be removed from the ribosome by treatment with EDTA or by acid elution followed by standard RNA purification using a kit (see Example 3) or by competitive elution using a soluble target molecule, followed by standard RNA purification using a kit.

Preferably and most advantageously, steps (a) to (c), are carried out two or more times prior to the identification step (d). This measure results in the less ambiguous identification of the desired nucleic acid with the concomitant minimization of false positive polysomes and thus nucleic acids. This embodiment for identifying the desired nucleic acid is particularly preferred, if several rounds of selection are necessary to isolate the specifically interacting (poly) peptide-target molecule pair.

In accordance with the present invention, it has surprisingly been found that by including antisense oligonucleotides complementary to the tag-coding sequence of ssrA-RNA results in a manifold increase in the efficiency of polysome display. This result is all the more unexpected since the prior art referred to above had already tried by various routes and means to establish such optimal conditions.

The present invention therefore provides a system for the phenotypic selection of target molecules such a ligands with (poly)peptides that are preferably complete, native protein molecules.

In a preferred embodiment of the present invention, the mRNA molecules comprise a stem loop at their 3' end.

In this embodiment of the invention, degradation of the mRNA by exonucleases is precluded to a significant extent.

Most preferably, a spacer is fused to the reading frame of the (poly)peptide to tether the emerging, folded (poly) peptide to the putative (poly)peptide channel of the ribosome. Said spacer preferentially encodes 57 to 116 amino acids.

Tethering of emerging (poly)peptide to the (poly)peptide channel of the ribosome is an additional advantageous means to enable co-selection of (poly)peptide and corresponding mRNA since it might significantly slow down the dissociation of the polysome.

In a further most preferred embodiment said stem loop region at the 3' end of the mRNA molecules encodes said spacer. Thereby, the length of the total 3' region can be kept to a minimum, if both spacer (required at the protein level) and stem loop (required at the RNA level) can be encoded by the same DNA.

A further preferred embodiment of the present invention relates to the above-recited method wherein said mRNA molecules comprise a stem loop structure at their 5' end.

Like the stem loop structure at the 3' end, the stem loop at the 5' end of the mRNA serves the purpose of avoiding a successful exonuclease attack towards the mRNA. It is particularly preferred that the mRNA comprises both a 5' and a 3' stem loop structure. In this embodiment, the mRNA molecule would structurally resemble natural mRNAs.

In an additional preferred embodiment of the method of the invention, said in vitro translation system is supplemented with inhibitors of ribonuclease.

Preferably, said ribonuclease inhibitors are transition state analogs and most preferably they are vanadyl ribonuclease complexes.

In accordance with the present invention, it was found that in particular vanadyl ribonuclease complexes may advantageously be used to further increase the efficiency of ribosome display. This result is particularly surprising since said complexes at the same time partially inhibit protein synthesis.

A further preferred embodiment of the invention relates to a method wherein the polysomes in steps (a) to (c) are stabilized by (a) the addition of magnesium salts, preferably magnesium acetate, after the formation of polysomes; and/or (b) a means that forms a bridge between the mRNA and the corresponding (poly)peptide; and/or (c) a low temperature after the translation and/or during the screening process.

The above recited means have been proven to further enhance the stability of the polysomes. Thus, a 50 mM magnesium acetate concentration in the reaction buffer significantly stabilized the ribosome complexes against dissociation.

The term "low temperature" in the above context is intended to mean a temperature that allows a successful screening to take place. Preferably said low temperature is in the range of 0 to 5° C.

Preferably, the translation is carried out in a prokaryotic translation system. Particularly preferred is an *E. coli* based translation system such as the S-30 *E. coli* translation system.

Alternatively, the translation system may be carried out in a eukaryotic translation system.

In a further preferred embodiment of the method of the present invention step (d) comprises
- (da) reverse transcribing said mRNA;
- (db) optionally amplifying the resulting cDNA;
- (dc) optionally cloning the optionally amplified cDNA; and
- (dd) determining the sequence of said cDNA.

This embodiment for identifying the nucleic acid of interest is preferred, if the population of mRNA molecules is too large to identify the desired species in a single round. Furthermore, it allows repeated and detailed testing of identified molecules, since the population of mRNA molecules becomes "immortalized" by cloning.

Reverse transcription allows sequencing using the most convenient DNA sequencing technology developed by Maxam and Gilbert as well as by Sanger and colleagues (see, e.g., Sambrook et al., "Molecular Cloning, A Laboratory Manual", second edition 1989, CSH Press, Cold Spring Harbor).

The amplification of cDNA, preferably by PCR, with or without subsequent cloning into a suitable vector, further significantly facilitates the identification of the desired nucleic acid molecule. In various cases, amplification of the nucleic acid molecule will be a prerequisite for allowing the investigator to subsequently identify said nucleic acid molecule.

In an additional preferred embodiment of the method of the invention, DNA is transcribed into mRNA in the presence of a reducing agent, such as β-mercaptoethanol and/or DTT, prior to step (a).

The inclusion of a reducing agent such as β-mercaptoethanol and/or DTT into the reaction buffer is known to increase the stability of DNA-polymerase. Accordingly, a reducing agent in the buffer contributes to an increase in the yield of mRNA which, in turn, results in an overall improvement of the ribosome display.

It is particularly preferred to remove said reducing agent after transcription and prior to step (a). This method of the invention is most preferred in cases where the (poly)peptide to be screened may comprise species that assume their native conformation by forming disulfide bridges. An example of such (poly)peptides are members of the immunoglobulin superfamily. By introducing this preferred embodiment, the present invention directly contradicts the prior art referred to above that suggests using a combined transcription/translation system.

Furthermore, the present invention also relates to a method for identifying a nucleic acid molecule encoding a (poly)peptide that interacts with a target molecule comprising the following steps:
- (a) transcribing a population of DNA molecules devoid of stop codons in the correct reading frame into the corresponding population of mRNA molecules in the presence of a reducing agent;
- (b) removing said reducing agent from said population of mRNA molecules;
- (c) translating said population of mRNA molecules in an in vitro translation system under conditions that allow the formation of polysomes;
- (d) bringing the polysomes so formed into contact with said target molecules under conditions that allow the interaction of the (poly)peptides encoded by said mRNA molecules and displayed by said polysomes with said target molecules;
- (e) separating polysomes displaying (poly)peptides that interact with said target molecules from polysomes displaying no such (poly)peptides; and
- (f) identifying the nucleic acid molecule encoding a (poly)peptide displayed in a polysome that interacts with said target molecules.

In a preferred embodiment the reducing agent used in step (a) is β-mercaptoethanol and/or DTT.

In a further preferred embodiment of the method of the present invention, the (poly)peptides comprise domains of the immunoglobulin superfamily, and preferably of the immunoglobulin family.

For example, said (poly)peptides may comprise complete T cell receptor or antibody chains or parts thereof such as domains of antibodies, for example the $V_H$ or $V_L$ regions.

It is particularly preferred that the (poly)peptides are single chain antibodies or fusion proteins comprising such single chain antibodies. In the latter alternative, the fusion partner of said antibody chains preferably is a tag that is employed for tethering the nascent (poly)peptide to the corresponding mRNA.

The present invention also preferably relates to a method wherein the translation system is supplemented with at least one compound selected from the group consisting of protein disulfide isomerase, oxidized or reduced glutathione, *E. coli* protein DsbA and molecular chaperones such as DnaK, DnaJ, GrpE, GroEL or GroES.

The above compounds, alone or in combination, may enhance the stability, solubility and/or native folding capacities of the nascent (poly)peptide.

The protein disulfide isomerase may be of bacterial or eukaryotic origin. The compound/enzyme that is included into the system would be selected by the person skilled in the art according to the type of protein that is screened. For example, if he screens a library comprising antibody domains he would, in accordance with the teachings of the present invention, include a eukaryotic protein disulfide isomerase. As could be shown by the present invention (see the appended examples) the polysome display system is significantly improved by incorporating said enzyme into the translation reaction system.

In a further preferred embodiment of the method of the present invention, non-specific interactions between the polysomes and/or the polysomes and the target molecules and/or, optionally, the polysomes and the matrix on which the target molecules are immobilized, formed during the step of bringing the polysomes into contact with said target molecules are inhibited or reduced by the addition of a blocking compound.

In a most preferred embodiment, said blocking compound is a polyanionic compound like heparin. Heparin has been suggested to be included as RNase inhibitor (WO 91/05058), but it has surprisingly been found in accordance with the present invention that it additionally decreases non-specific binding. It can be assumed that heparin as polyanionic compound competes with the polyanionic mRNA as part of the polysome complexes for non-specific binding sites, rendering the addition of polyanionic compounds such as heparin in polysome display a generally applicable method for decreasing non-specific binding.

In another most preferred embodiment, said blocking compound is sterilized milk. The addition of nonfat milk has already been suggested for polysome display (WO 95/11922). However, according to the present invention it has been found that no RNA could be isolated when milk was used during affinity selection. Surprisingly, when sterilized milk was used, RNA isolation was again possible, and the amount of non-specific binding was substantially decreased.

Furthermore, the present invention relates to a kit comprising (a) antisense oligonucleotides complementary to the tag-coding sequence of ssrA-RNA;

(b) optionally a vector suitable for cloning nucleic acids encoding (poly)peptides to be screened;

(c) optionally, ribonuclease inhibitors, preferably transition state analogs, and most preferably vanadyl ribonucleoside complexes;

(d) optionally, at least one compound selected from the group consisting of a protein disulfide isomerase, oxidized or reduced glutathione, E. coli DsbA, and molecular chaperones; and (e) optionally oligonucleotides encoding 5' or 3' stem loops, spacers or terminators without stop codons.

In a preferred embodiment the kit according to the invention may furthermore comprise:

(f) S-30 translation extract;

(g) PCR components;

(h) reverse transcriptase;

(i) an RNA sequencing kit;

(j) a DNA sequencing kit, either alone or in combination.

Finally, the present invention relates to a kit comprising (a) an in vitro cell-free translation extract free of ssrA-RNA;

(b) optionally a vector suitable for cloning nucleic acids encoding (poly) peptides to be screened;

(c) optionally, ribonuclease inhibitors, preferably transition state analogs, and most preferably vanadyl ribonucleoside complexes;

(d) optionally, at least one compound selected from the group consisting of a protein disulfide isomerase, oxidized or reduced glutathione, E. coli DsbA, and molecular chaperones; and (e) optionally oligonucleotides encoding 5' or 3' stem loops, spacers or terminators without stop codons.

In a preferred embodiment the kit according to the invention may furthermore comprise:

(f) PCR components;

(g) reverse transcriptase;

(h) an RNA sequencing kit;

(i) a DNA sequencing kit, either alone or in combination.

The kit of the present invention can conveniently be used to carry out the method of the present invention.

BRIEF DESCRIPTION OF THE DRAWINGS

The figures show:

FIG. 1 Principle of in vitro ribosome display for screening native protein (scFv) libraries for ligand (antigen) binding. 1, a DNA scFv library is first amplified by PCR, whereby a T7 promoter, ribosome binding site and stem loops are introduced, and then transcribed to RNA. 2, after purification, mRNA is translated in vitro in an E. coli S-30 system in the presence of different factors enhancing the stability of ribosomal complexes and improving the folding of the scFv antibodies on the ribosomes. Translation is stopped by cooling on ice, and the ribosome complexes are stabilized by increasing the magnesium concentration. 3, the desired ribosome complexes are affinity selected from the translation mixture by binding of the native scFv to the immobilized antigen. Unspecific ribosome complexes are removed by intensive washing. 4, the bound ribosome complexes can then be dissociated by EDTA (4b), or whole complexes can be specifically eluted with antigen (4a). 5, RNA is isolated from the complexes. 6, Isolated mRNA is reverse transcribed to cDNA, and cDNA is then amplified by PCR. This DNA is then used for the next cycle of enrichment, and a portion can be analyzed by cloning and sequencing and/or by ELISA or RIA.

FIG. 2 (Panels A–C) (A) Schematic drawing of the scFv construct used for ribosome display. T7 denotes the T7 promoter, SD the ribosome binding site, F the 3 amino acid long FLAG (Knappik, A. & Plückthun, A. (1994) BioTechniques 17, 754–761) with N-terminal methionine, $V_L$ and $V_H$ the variable domains of the scFv fragment, L the linker, spacer the part of protein construct connecting the folded scFv to the ribosome, 5'sl and 3'sl the stem loops on the 5'- and 3'-ends of the mRNA. The arrow indicates the transcriptional start. The strategy for the PCR amplification is shown.

(B) The amount of the scFvhag mRNA bound to the polysome complexes is influenced by the secondary structure of its ends and the length of the spacer connecting the folded scFv to the ribosome. Different constructs of scFvhag mRNA were used for one cycle of ribosome display (constructs c1–c9). None of them contained a stop codon. Each species was tested separately. After affinity selection of the ribosome complexes from 100 μl of translation mixtures, mRNAs were isolated and analyzed by Northern hybridization. The presence of the 5' stem loop is labeled (+) or (–), that of the 3' stem loop is labeled as (–) when absent, (l) when derived from the lpp terminator or (t) when derived from the T3Te terminator. The spacer length indicates the number of amino acids following the scFv and connecting it to the ribosome, including the translated stem loop. The lengths of RNA in kb is derived from RNA molecular weight marker III (Boehringer Mannheim). The bar graph shows the quantified amounts of mRNA from fluoroimager analysis.

(C) Effect of additives on the amount of mRNA bound to the ribosome complexes. The mRNA of the scFvhag construct c7 was used for one cycle of ribosome display. Samples in FIG. 2B lane c7 and FIG. 2C lane 6 are identical. When indicated, 3.5 mM anti-ssrA oligonucleotide ON10 (SEQ ID NO: 2) (5'-TTAAGCTGCTAAAGCGTAGTTTT-CGTCGTTTGCGACTA-3'), 35 mg/ml protein disulfide isomerase (PDI) or 1 mg/ml vanadyl ribonucleoside complexes (VRC) was included in the translation. Translations were stopped by addition of Mg(Ac)$_2$ to the final concentration indicated (in mM) and by cooling on ice. After affinity selection of the ribosome complexes from 100 μl of translation mixtures mRNAs were isolated and analyzed by Northern hybridization. The bar graph shows the quantified amounts of mRNA from fluoroimager analysis.

FIG. 4 (Panels A–B) (A) Enrichment of the scFvhag ribosome complexes from mixtures with scFvAL2 by ribosome display. mRNA of scFvhag c5 was diluted $10_8$ times with mRNA of scFvAL2, and the mixture was used for ribosome display. After affinity selection of scFvhag ribosome complexes, mRNA was isolated, reverse transcribed to cDNA using oligonucleotide ON5 (SEQ ID NO: 7), cDNA was amplified by PCR using oligonucleotides ON3 (SEQ ID NO: 5) and ON7 (SEQ ID NO: 9) and analyzed by agarose electrophoresis. Lanes 1–5 are PCR products amplified after the 1st to 5th cycles of the ribosome display, respectively. M is the 1 kb DNA ladder (Gibco BRL) used as MW marker. PCR products corresponding to scFvhag and scFvAL2 are labeled.

(B) Enrichment of either scFvhag c5 or scFvAL2 ribosome complexes by ribosome display as a function of immobilized antigen. mRNAs of scFvhag and scFvAL2 were mixed in a 1:1 ratio and used for one cycle of ribosome display. After affinity selection, mRNA was isolated, reverse transcribed, amplified by PCR and analyzed by agarose electrophoresis as in FIG. 4A. The same 1:1 mixture was affinity selected on immobilized transferrin (tr) as a control, ampicillin-transferrin conjugate (amp), or hag-peptide-transferrin-conjugate (hag). PCR products corresponding to scFvhag and scFvAL2 are labeled.

FIG. 5 (Panels A–C) (A) Analysis of RNA pool after the $3^{rd}$ round of polysome display: in vitro translation of RNA pool and RIA assay of labelled polysome complexes in the presence of 2% milk: (a) binding to BSA; (b) binding to BSA-GCN4 (7P14P) (SEQ ID NO: 13); (c) binding to BSA-GCN4 (7P14P) (SEQ ID NO: 13) on inhibition with 1 $\mu$M GCN4 (7P14P) (SEQ ID NO: 13); (d) binding to BSA-GCN4 (7P14P) (SEQ ID NO: 13) on inhibition with 1 $\mu$M hag peptide; (e) binding to BSA-GCN4 (7P14P) (SEQ ID NO: 13) on inhibition with 1 $\mu$M fluorescein.

(B) Analysis of RNA pool after the $3^{rd}$ round of polysome display: in vitro translation of RNA pool and RIA assay of labelled polysome complexes in the absence of 2% milk: (a) binding to BSA; (b) binding to BSA-GCN4 (7P14P) (SEQ ID NO: 13); (c) binding to BSA-GCN4 (7P14P) (SEQ ID NO: 13) on inhibition with 1 $\mu$M GCN4 (7P14P) (SEQ ID NO: 13); (d) binding to BSA-GCN4 (7P14P) (SEQ ID NO: 13) on inhibition with 1 $\mu$M hag peptide; (e) binding to BSA-GCN4 (7P14P) (SEQ ID NO: 13) on inhibition with 1 $\mu$M fluorescein.

(C) Analysis of RNA pool after the $3^{rd}$ round of polysome display by RIA: RNA pool after 3 rounds of affinity selection performed in the absence of milk (A), or in the presence of milk (B):

in vitro translation of RNA pool and binding assay of labelled polysome complexes in the presence of 2% milk: (a) binding to BSA-GCN4 (7P14P) (SEQ ID NO: 13); (b) binding to BSA-GCN4 (7P14P) (SEQ ID NO: 13) on inhibition with 1 $\mu$M GCN4 (7P14P) (SEQ ID NO: 13).

DETAILED DESCRIPTION OF THE INVENTION

The examples illustrate the invention.

In the appended examples, it is shown that an scFv fragment of an antibody, which requires its correctly assembled three-dimensional structure to bind the antigen (a hydrophilic peptide), can be enriched $10^8$-fold by ribosome display and its sequence "evolves" during the process.

EXAMPLE 1

Construction of scFv Antibody Fragments

The scFvhag construct c7 was amplified by PCR in two steps from an fd phage displaying the scFv 17/9 (Schulze-Gahmen, U., Rini, J. M. & Wilson, I. A. (1993) *J. Mol. Biol.* 234, 1098–1118; Krebber, C., Spada, S., Desplancq, D. & Plückthun, A. (1995) *FEBS Lett.* 377, 227–231) containing a (Gly4Ser)$_3$ (SEQ ID NO: 12) linker, using in the first step oligonucleotides ON1 (SEQ ID NO: 3) (5'-TTTCCCGAATTGTGAGCGGATAACAATAGAAA-TAATTTTGTTTAACTTTAAGAA GGAGATATATC-CATGGACT ACAAAGA-3'), which introduces a ribosome binding site (RBS), and ON2 (SEQ ID NO: 4) (5'-TTTAAGCAG CTCGATAGCAGCAC-3'). In the second step ON3 (SEQ ID NO: 5) (5'-ATATATGTCGACGAAAT-TAATACGACTCACTATAG GGAGACCACAACG-GTTTC CCGAATTGTG-3'), which introduces the T7 promoter and the 5'-loop, and ON4 (SEQ ID NO: 6) (5'-AGACCCGTTTAGAGGCCCC AAGGGGTTATGGAA-TTCACCTTTAAGCAGCT C-3'), which introduces a modified lpp terminator loop with stop codon removed, were used. The spacer, fused C-terminally to the scFv, is derived from amino acids 211 to 299 of gene III of filamentous phage M13mp19 (Krebber, C., Spada, S., Desplancq, D. & Plückthun, A. (1995) *FEBS Lett.* 377, 227–231), and the translated lpp terminator adds another 24 amino acids.

The other constructs were prepared by PCR from c7 using the following primer pairs: c1, ON5 (SEQ ID NO: 7) (5'-TCAGTAGCGACAGAATCAAG-3') and ON6 (SEQ ID NO: 8) (5'-GAAATTAA TACGACTCACTATAGGGT-TAACTTTAGAAGGAGGTATATCCATGGACTACAAA GA-3'), which introduces the T7 promoter and RBS without the 5'-stemloop, the spacer is derived from amino acids 211–294 of gene III; c2, ON4 (SEQ ID NO: 6) and ON6 (SEQ ID NO: 8), the same spacer as c7; c3, ON6 (SEQ ID NO: 8) and ON7 (SEQ ID NO: 9) (5'-GGCCCACCCGTGAA GGTGAGCCTCAGTAGCGA-CAG-3'), the spacer is derived from amino acids 211–294 of gene III following 7 amino acids of the translated T3Te terminator; c4, ON3 (SEQ ID NO: 5) and ON5 (SEQ ID NO: 7), the same spacer as c1; c5, ON3 (SEQ ID NO: 5) and ON7 (SEQ ID NO: 9), the same spacer as c3; c6, ON2 (SEQ ID NO: 4) and ON3 (SEQ ID NO: 5), the spacer is derived from amino acids 211–299 of gene III following the first 4 amino acids of the lpp terminator; c8, ON3 (SEQ ID NO: 5) and ON8 (5'-TTTAAGCAGCTCATCAAA ATCACC-3') (SEQ ID NO: 10), the spacer is derived from amino acids 211–264 of gene III following the first 4 amino acids of the lpp terminator; c9, ON3 (SEQ ID NO: 5) and ON4 (SEQ ID NO: 6), the spacer is derived from amino acids 211 to 264 of gene III following 24 amino acids of the lpp terminator, using construct c8 as a template.

The scFvAL2 construct (V$_L$-(Gly4Ser)$_4$- V$_H$) (SEQ ID NO: 12) was amplified by PCR in two steps from plasmid pAK202 (Krebber, A., Bornhauser, S., Burmester, J., Honegger, A., Willuda, J., Bosshard, H. R. & Plückthun, A. (1997) *J. Immunol. Meth.* 201, 35–55), using first oligonucleotides ON1 (SEQ ID NO: 3) and ON7 (SEQ ID NO: 9) and in the second step ON3 (SEQ ID NO: 5) and ON7 (SEQ ID NO: 9). The spacer is derived from amino acids 240 to 294 of gene III of filamentous phage M13mp19 (Krebber, A., Bornhauser, S., Burmester, J., Honegger, A., Willuda, J., Bosshard, H. R. & Plückthun, A. (1997) *J. Immunol. Meth.* 201, 35–55), and the translated T3Te terminator adds another 7 amino acids.

EXAMPLE 2

RT-PCR and in vitro Transcription

Reverse transcription was performed using Superscript reverse transcriptase (Gibco BRL) according to the manufacturer's recommendation. PCR was performed using Taq polymerase (Gibco BRL) in the presence of 5% DMSO (4 min at 94° C., followed by 3 cycles of 30 sec at 94° C., 30 sec at 37° C., 2 min at 72° C., followed by 10 similar cycles at 60° C. instead of 37° C., 20 similar cycles at 60° C. instead of 37° C. with elongation at 72° C. prolonged by 15 sec per cycle and finished by 10 min at 72° C.). PCR products were analyzed by agarose gel electrophoresis and purified from the gel and reamplified, if the amount and quality was not sufficient, or directly used for transcription without additional purification. In vitro transcription was performed as described (Pokrovskaya, I. D. & Gurevich, V. V. (1994) Anal. Biochem. 220, 420–423).

EXAMPLE 3

Model System and Quantification of Yields of Affinity Selection

As a model system, we used single-chain Fv (scFv) fragments of antibodies (Huston, J. S., Levinson, D., Mudgett-Hunter, M., Tai, M. S., Novotny, J., Margolies, M. N., Ridge, R. J., Bruccolleri, R. E., Haber, E., Crea, R. & Oppermann, H. (1988) Proc. Natl. Acad. Sci. U.S.A. 85, 5879–5883), in which the variable domain of the light chain ($V_L$) is connected via a flexible linker to the variable domain of the heavy chain ($V_H$). To tether the folded protein to the ribosome and not interfere with folding we fused a spacer to the C-terminus of the scFv fragment. Since the antibody domains form disulfide bonds, and the RNA polymerase requires β-mercaptoethanol for maximal stability, the effect of performing transcription in a separate reaction was investigated. Further, the conditions for oxidative protein folding during translation (Ryabova, L., Desplancq, D., Spirin, A. & Plückthun, A. (1997) Nature Biotechnology, 15, 79–84) were optimized (see below).

Polypeptide release is an active process, requiring three polypeptide release factors in E. coli (Grentzmann, G., Brechemier-Baey, D., Heurgue-Hamard, V. & Buckingham, R. H. (1995) J. Biol. Chem. 270, 10595–10600; Tuite, M. F. & Stansfield, I. (1994) Mol. Biol. Rep. 19, 171–181; Tate, W. P. & Brown, C. M. (1992) Biochemistry 31, 2443–2450) and one ribosome recycling factor which releases the mRNA (Janosi, L., Shimizu, I. & Kaji, A. (1994) Proc. Natl. Acad. Sci. U.S.A. 91, 4249–4253). The consequence of release factor binding is normally the hydrolysis of the peptidyl tRNA between the ribose and the last amino acid by the peptidyl transferase center of the ribosome (Tate, W. P. & Brown, C. M. (1992) Biochemistry 31, 2443–2450). Our system is devoid of stop codons, and thus a fraction of the polypeptide may not be hydrolyzed off the tRNA and remain attached to the ribosome and thus be available for affinity selection.

In vitro translation in an E. coli S-30 system was performed according to Chen and Zubay (Chen, H. Z. & Zubay, G. (1983) Methods Enzymol. 101, 674–690) with several modifications. Translation was carried out for 10 min at 37° C. in a 110 μl reaction which contained the following components: 50 mM Tris-Ac, pH 7.5, 30 mM NH4Ac, 12.3 mM Mg(Ac)2, 0.35 mM of each amino acid, 2 mM ATP, 0.5 mM GTP, 1 mM cAMP, 0.5 mg/ml E. coli tRNA, 20 μg/ml folinic acid, 100 mM KAc, 30 mM acetylphosphate (Ryabova, L. A., Vinokurov, L. M., Shekhotsova, E. A., Alakhov, Y. B. & Spirin, A. S. (1995) Anal. Biochem. 226, 184–186), 1.5% PEG 8000, 33 μg/ml rifampicin, 1 mg/ml vanadyl ribonucleoside complexes (VRC), 23 μl of E. coli MRE600 extract (Chen, H. Z. & Zubay, G. (1983) Methods Enzymol. 101, 674–690) and 90 μg/ml of mRNA.

Figure 1:
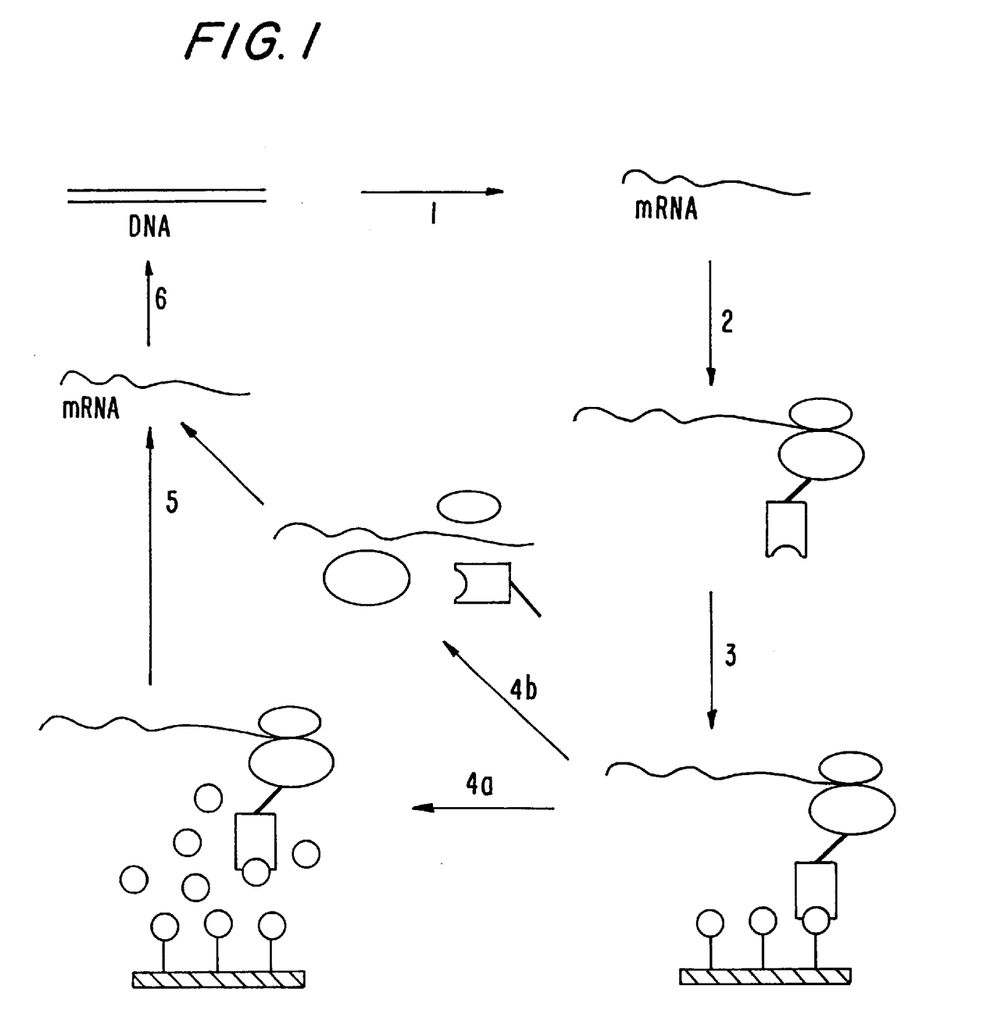

Translation is stopped by cooling on ice, and the ribosome complexes are further stabilized against dissociation by 50 mM magnesium acetate (Holschuh, K. & Gassen, H. G. (1982) J. Biol. Chem. 257, 1987–1992). Chloramphenicol at 50 μM concentration, assumed to also induce ribosome stalling (Mattheakis, L. C., Bhatt, R. R. & Dower, W. J. (1994) Proc. Natl. Acad. Sci. U.S.A. 91, 9022–9026; Moazed, D. & Noller, H. F. (1987) Nature 327, 389–394), did not improve the selection properties (data not shown). The whole complex, consisting of synthesized protein, ribosome and mRNA was then bound to the affinity matrix, washed and eluted with competing ligand, or the ribosomes were dissociated with EDTA (FIG. 1). In particular, the samples were diluted four-fold with ice-cold washing buffer (50 mM Tris-Ac pH 7.5, 150 mM NaCl, 50 mM Mg(Ac)$_2$ and 0.1% Tween-20) and centrifuged for 5 min at 4° C. at 10.000×g to remove insoluble components. Microtiter plates coated with hag-transferrin conjugate were prewashed with ice-cold washing buffer, and the supernatant from the centrifuged translation mixture was applied (200 μl per microtiter well) and the plate was gently shaken for 1 hour in the cold room. After 5 washes with ice-cold washing buffer, the retained ribosome complexes were dissociated with ice-cold elution buffer (100 μl per well; 50 mM Tris-Ac, pH 7.5, 150 mM NaCl, 10 mM EDTA, 50 μg/ml of E. coli tRNA) for 10 min in the cold room, and released mRNA was recovered by ethanol precipitation or by isolation using the Rneasy kit (Qiagen).

We did not find it necessary to preparatively isolate polysomes at any stage. The efficiency of ribosome display was found to be two orders of magnitude lower when using a coupled in vitro transcription-translation (data not shown).

We developed the ribosome display system in two stages, first by engineering the gene structure for in vitro transcription, translation and folding, then by optimizing the translation reaction itself. Each test started with 10 μg of input mRNA; this corresponds to ~1.5×10$^{13}$ molecules. The input mRNA was subjected to a single round of affinity selection: translation in vitro, capture of ribosome complexes on immobilized target ligand and release of mRNA. The released mRNA was then quantified by Northern analysis.

For Northern analysis, RNA electrophoresis and transfer to a Nytran membrane (Schleicher & Schuell) were carried out as described (Goda, S. K. & Minton, N. P. (1995) Nucleic Acids Res. 23, 3357–3358) with a Turboblotter (Schleicher & Schuell). Hybridization was performed for 12 hours at 60° C. (Church, G. M. & Gilbert, W. (1984) Proc. Natl. Acad. Sci. U.S.A. 81, 1991–1995). Hybridization was carried out with the oligonucleotide ON9 (5'-ACATGGTAACTTTTTCACCAGCGGTAACGG-3') (SEQ ID NO: 11), which anneals to the $V_L$ region of scFvhag mRNA. This oligonucleotide was labeled by 3' tailing with digoxigenin-11-dUTP/dATP using the DIG Oligonucleotide Tailing Kit (Boehringer Mannheim). Washing conditions were as follows: 2×SSC, 0.5% SDS for 5 min at room temperature; 2×SSC, 0.5% SDS for 2×30 min at 60° C.; 0.1×SSC for 10 min at room temperature. The hybridized oligonucleotide probe was detected using the DIG DNA Labeling and Detection Kit with the chemiluminescent substrate CSPD (Boehringer Mannheim) and exposure to X-ray film, or with the fluorimetric substrate Attophos (Boehringer Mannheim) and analysis using a fluoroimager (Molecular Dynamics).

EXAMPLE 4

Effect of mRNA Structure on Yield

Figure 2A:
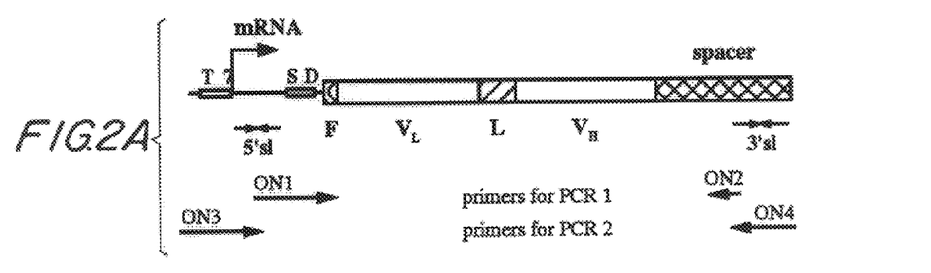

In designing the ribosome display system, we first engineered the flanking regions of the scFv gene (FIG. 2A). The gene should be transcribed very efficiently from the PCR product, and its mRNA should be stable against nucleases.

Figure 2B:
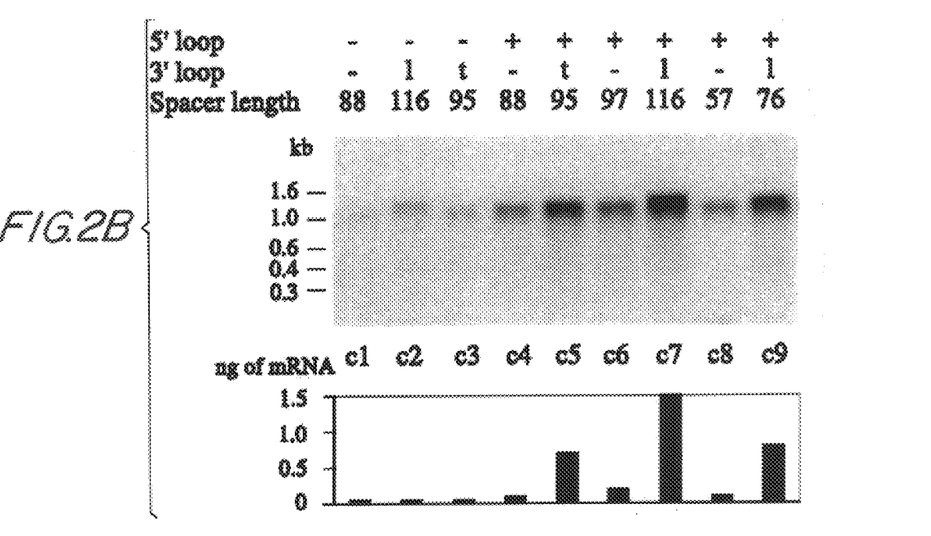

For the 5' end, we used the T7 promoter and the natural T7-gene10 upstream region, which encodes a stemloop structure directly at the beginning of the mRNA (Studier, F. W., Rosenberg, A. H., Dunn, J. J. & Dubendorff, J. W. (1990) *Methods Enzymol.* 185, 60–89). At the 3' end, we fused a spacer region of 57–116 amino acids to the reading frame of the scFv to tether the emerging, folded polypeptide to the putative polypeptide channel of the ribosome and to give it enough distance to not interfere with folding. This spacer encodes at the RNA level a 3' stemloop, either the terminator of the *E. coli* lipoprotein (Studier, F. W., Rosenberg, A. H., Dunn, J. J. & Dubendorff, J. W. (1990) *Methods Enzymol.* 185, 60–89) (lpp term) or the early terminator of phage T3 (Reynolds, R., Bermudez-Cruz, R. M. & Chamberlin, M. J. (1992) *J. Mol. Biol.* 224, 31–51) (T3Te), to increase the stability of mRNA against exonucleases. In a direct comparison of flanking regions (FIG. 2B) after one round of translation and selection, we obtained the best result for constructs possessing a 5'-loop (from T7-g10), a 3'-loop (from the lpp terminator) and the longest spacer of 116 amino acids. The yield of mRNA after one round of ribosome display improved from less than 0.001% of input mRNA to 0.015% (15 times).

EXAMPLE 5

Effect of Translation Conditions on Yield

Figure 2C:
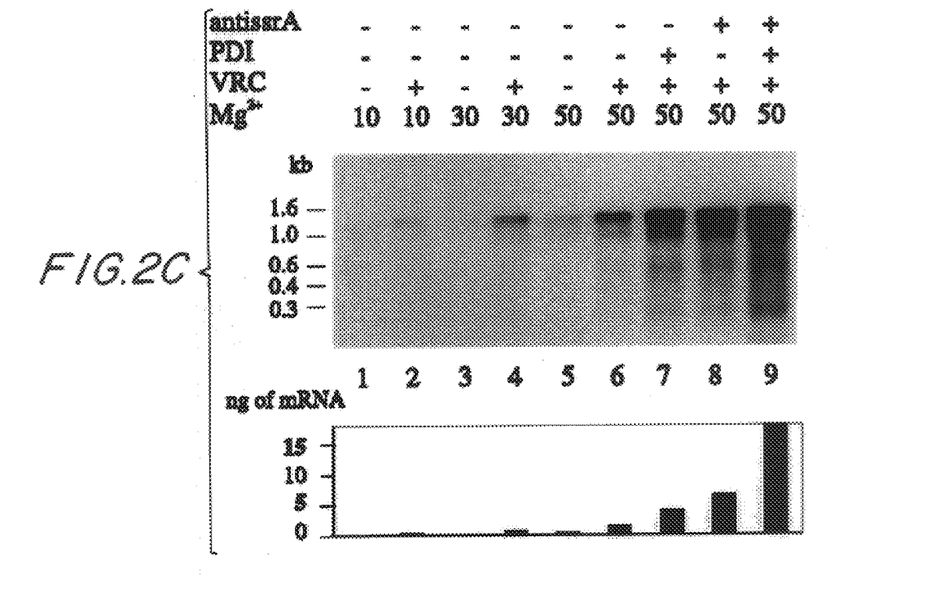

We then tested the effect of various compounds present during translation. Nucleases were found to be efficiently inhibited by vanadyl ribonucleoside complexes (VRC), which should act as transition state analogs (Berger, S. L. (1987) *Methods Enzymol.* 152, 227–234). VRC at 1 mg/ml maximized the yield of isolated mRNA from ribosome complexes after one round of affinity selection when it was present during translation (FIG. 2C), even though protein synthesis was partially inhibited (data not shown), and omitting VRC led to a several-fold decreased efficiency of the ribosome display (FIG. 2C). In contrast, Rnasin (Mattheakis, L. C., Bhatt, R. R. & Dower, W. J. (1994) *Proc. Natl. Acad. Sci. U.S.A.* 91, 9022–9026) had no effect on the efficiency of the system. We did not find evidence for significant proteolytic degradation of the scFv synthesized under these conditions, since prolonged incubation of released product (up to 300 min) did not alter the electrophoretic pattern (data not shown).

From a systematic study on the in vitro translation of soluble scFv fragments in the presence of molecular chaperones and disulfide forming catalysts (Ryabova, L., Desplancq, D., Spirin, A. & Plückthun, A. (1997) *Nature Biotechnology*, 15, 79–84), we found that binding activity is obtained if and only if disulfide formation and rearrangement is allowed to take place during translation and folding. The strong beneficial effect of protein disulfide isomerase (PDI) was verified for the ribosome display system, in which the protein is not released. It can be seen that PDI improves the performance of the ribosome display for scFv fragments three-fold (FIG. 2C), and thus catalyzes the formation and isomerization of disulfide bonds on the ribosome-bound protein.

Figure 3:
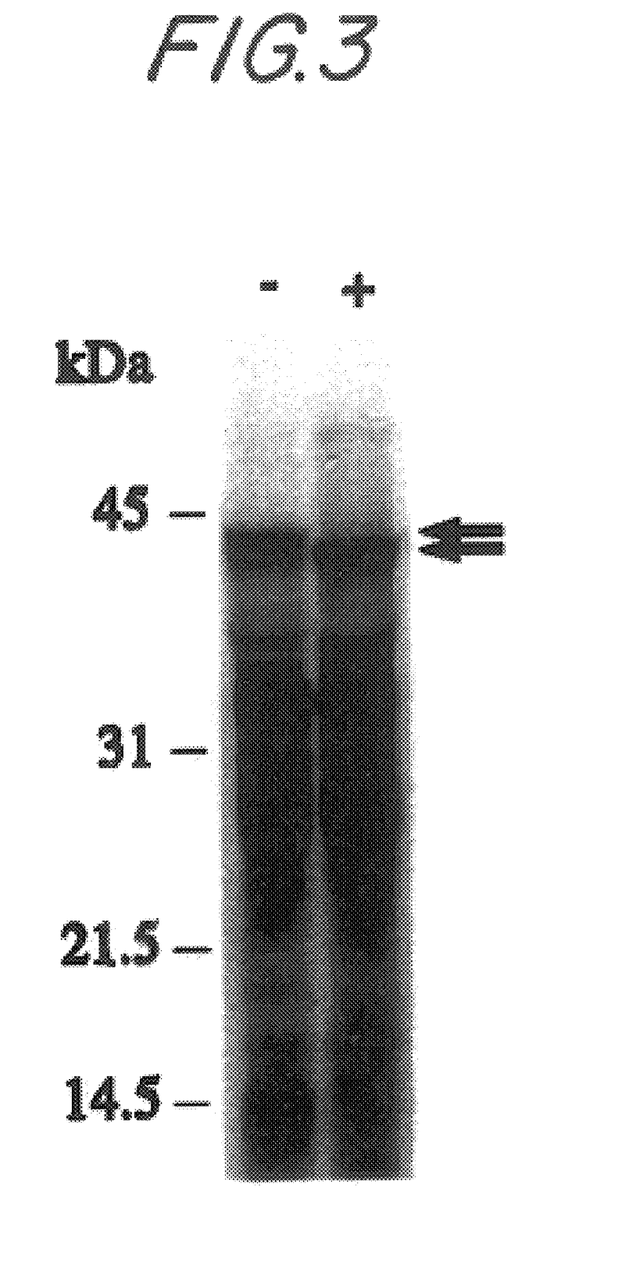
FIG. 3 Anti-ssrA antisense oligonucleotide ON10 (SEQ ID NO: 2) (FIG. 2C) decreases the molecular mass of the longest protein species (arrows). In vitro translation was performed using $^{35}$S-methionine and scFvhag c7 mRNA. Reactions were carried out in the absence (–) or presence (+) of 3.5 mM oligonucleotide ON10 (SEQ ID NO: 2). An SDS-PAGE of translation products is shown.

Recently, a peptide tagging system was discovered in *E. coli*, whereby proteins translated from mRNA, devoid of a stop codon, are modified and released from the ribosomes by the addition of a C-terminal tag, encoded by ssrA-RNA, and thereby marked for degradation (Keiler, K. C., Waller, P. R. & Sauer, R. T. (1996) *Science* 271, 990–993). It is shown in the present invention that this degradation could be inhibited by an antisense oligonucleotide complementary to the tag-coding sequence of ssrA-RNA. It was further surprising to observe that such a possible inhibition had an effect on the ribosome display. Indeed, a four-fold higher efficiency of ribosome display is visible in the presence of anti-ssrA oligonucleotide (FIG. 2C), and the MW of the longest protein product is decreased, presumably by preventing the attachment of the degradation tag (FIG. 3). Combining PDI and the anti-ssrA oligonucleotide led to a twelve-fold increased efficiency of the ribosome display system (FIG. 2C).

By the combination of proper mRNA secondary structure and various compounds present during translation we could increase the yield of mRNA after one round of affinity selection 200 times—from less than 0.001% to 0.2% of input mRNA. This number expresses the combined efficiency of covalent attachment to the ribosome, protein folding, ligand binding, ribosome capture and RNA release and amplification.

EXAMPLE 6

Specific Enrichment of Target mRNA Through Multiple Rounds of Selection

Figure 4A:
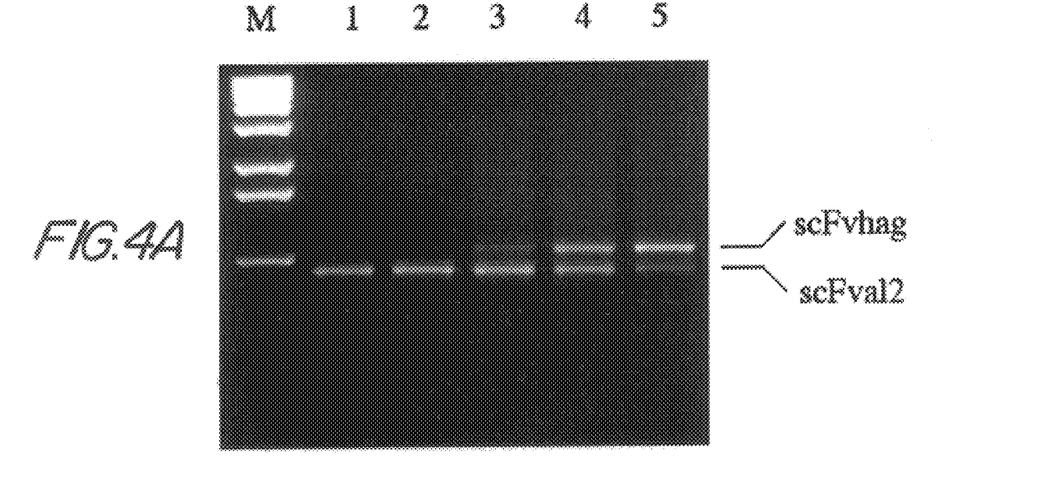

In a test of the optimized system, we investigated how well a mixture of two proteins can be enriched for function. Two scFv antibody mRNAs, constructed identically according to FIG. 2A, both possessing the 5' and the 3' T3Te loop, one encoding the anti-hemagglutinin scFv 17/9 (Schulze-Gahmen, U., Rini, J. M. & Wilson, I. A. (1993) *J. Mol. Biol.* 234, 1098–1118) (scFvhag), the other the anti-beta-lactam antibody AL2 (Krebber, A., Bornhauser, S., Burmester, J., Honegger, A., Willuda, J., Bosshard, H. R. & Plückthun, A. (1996) *J. Immunol. Meth.*, in press) (scFvAL2), were mixed at a ratio of $1:10^8$. Their PCR products differ slightly in length, because of differences mainly in the spacer length, and can thus easily be distinguished (FIG. 4A). After 5 cycles according to FIG. 1, undergoing selection on immobilized hag-peptide, 90% of the ribosome complexes contained scFvhag. We can thus conclude that the enrichment is about 2 orders of magnitude per cycle under these conditions.

Figure 4B:
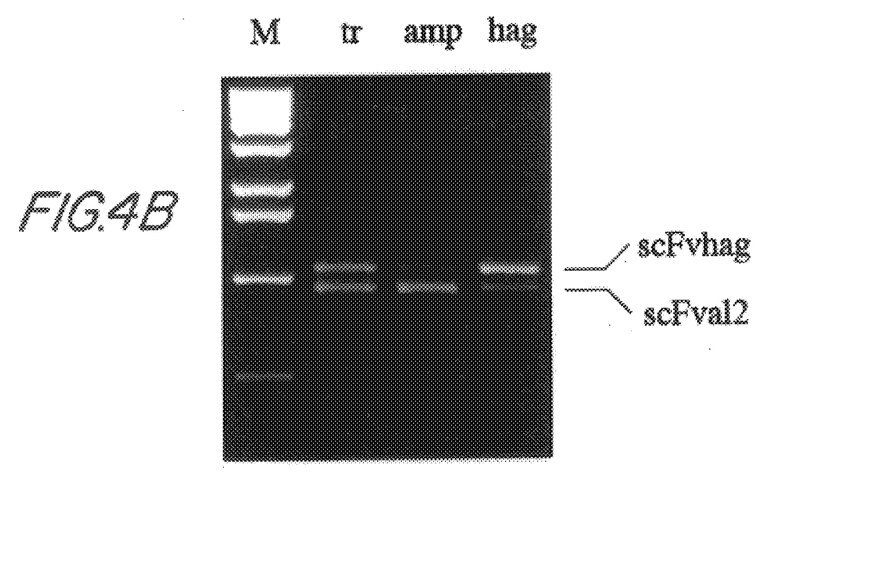

To verify that enrichment really occurred through affinity selection, we tested enrichment of a 1:1 mixture of both mRNAs on an irrelevant surface and saw no change from the input ratio (FIG. 4B). Furthermore, from the identical 1:1 mRNA mixture either antibody could be enriched, depending on which antigen was immobilized (FIG. 4B).

EXAMPLE 7

Analysis of scFv Antibody Fragments After Affinity Selection

After the 5th round of selection, the PCR products were ligated into a vector, transformed into *E. coli* and single clones were analyzed. The experimental protocol was as follows: After the 5th round of ribosome display PCR products were cloned into the vector pTFT74 (Ge, L., Knappik, A., Pack, P., Freund; C. & Plückthun, A. (1995) in *Antibody Engineering*, eds. Borrebaeck, C. A. K. (Oxford University Press, New York), In vitro coupled transcription-translation in the S-30 *E. coli* system was performed using 50 μg/ml of plasmid DNA under similar conditions as described above with the following modifications. A coupled transcription-translation was carried out for 30 min at 37° C., and the reaction mixture was supplemented with 2000 U/ml of T7 RNA polymerase and 0.5 mM UTP and TTP. The mixture contained 50 μCi/ml of 35S-methionine and 0.35 mM of each amino acid except methionine. After translation, the reaction mixture was diluted four-fold with PBS and bound to immobilized hag-peptide in a microtiter well. After 60 min incubation with gentle shaking, microtiter wells were washed 5 times with PBST and bound radioactive protein was eluted with 0.1 M triethylamine. Eluted protein was quantified in a scintillation counter. Of 20 clones sequenced, 18 had the scFvhag sequence, and 2 had the scFvAL2 sequence, demonstrating that the $10^8$ fold enrichment was successful. Of the 18 scFvhag clones, 13 gave ELISA signals within 43–102% of wild-type, inhibitable by soluble hag peptide, 2 were reduced to 14 and 18%, and 3 were significantly reduced in binding (less than 10%), probably a result of errors introduced during the last round of PCR amplification (Table 1). Thus, the selective pressure to maintain antigen binding, executed by binding and elution from immobilized antigen, is clearly operating, albeit in the context of an ongoing genetic diversification through PCR errors.

The sequence analysis showed that the clones contained between 3 and 7 base changes, with 90% transitions and 10% transversions, in good agreement with the known error properties of Taq polymerase (Keohavong, P. & Thilly, W. G. (1989) *Proc. Natl. Acad. Sci. U.S.A.* 86, 9253–9257). Each clone has gone through a total of 165 cycles of PCR, interrupted by 5 phenotypic selections for binding, and an error rate of $3.3 \times 10^{-5}$ can be calculated under these conditions, where only mutations which have survived the selection are counted.

At the protein level, the selected clones carry between 0 and 4 exchanged amino acids, distributed over $V_L$, $V_H$ and the linker. All mutations are independent of each other (Table 1) and give therefore an indication of a large range of neutral mutations compatible with function, and perhaps even of improvements the system has selected for. While the exact properties of the selected molecules requires further analysis, we note the selection of a proline at the beginning of the linker, which may facilitate the required turn formation (Tang, Y., Jiang, N., Parakh, C. & Hilvert, D. (1996) *J. Biol. Chem.* 271, 15682–15686) and the selection of acidic residues, which are known to increase solubility (Dale, G. E., Broger, C., Langen, H., D'Arcy, A. & Stüber, D. (1994) *Protein Eng.* 7, 933–939; Knappik, A. & Plückthun, A. (1995) *Protein Eng.* 8, 81–89).

EXAMPLE 8

Construction of Polysome Display Library

We constructed a library of scFvs in the orientation VL-VH with the two domains being connected by a $(Gly_4Ser)_4$ (SEQ ID NO: 12) linker. To introduce a spacer, a protein tethering an scFv to the ribosome and allowing to fold an scFv on it, we first ligated the library to the vector pAK200 (Krebber, A., Bornhauser, S., Burmester, J., Honegger, A., Willuda, J., Bosshard, H. R. & Plückthun, A. (1997) *J. Immunol. Meth.* 201, 35–55) which resulted on the protein level in scFvs fused to the C-terminal part of gene III of filamentous phage M13mp19. In the second step we introduced stem loops, which stabilize mRNA against RNases, and the other important features by PCR. The final library construct contained a T7 promoter, 5'-stem loop and Shine-Dalgarno sequence upstream of the scFv coding sequence and a spacer consisting of 129 bases of gene III filamentous phage M13mp19 (amino acids 250–293) following by 21 bases of translated early terminator of phage T3 (T3Te), introducing as well a 3'-stemloop, downstream of scFv.

Cloning of the library followed the methods described in literature (Krebber, A., Bornhauser, S., Burmester, J., Honegger, A., Willuda, J., Bosshard, H. R. & Plückthun, A. (1997) *J. Immunol. Meth.* 201, 35–55). In short, mRNA was extracted from spleen cells of 6 mice immunized with either GCN4(7P14P) peptide (RMKQLEPKVEELLPKNYHL-ENEVARLKKLVGER)(SEQ ID NO: 13) coupled to KLH or biotinylated GCN4(7P14P) (SEQ ID NO: 13) coupled to avidin, and transcribed to cDNA using random hexamer primers. After VL and VH PCR amplification followed by assembly PCR, PCR products were directly diluted 3× in SfiI reaction buffer, digested and separated using agarose gel electrophoresis. SfiI digested DNAs were extracted from agarose gel by Amicon spin columns, concentrated by isopropanol precipitation and dissolved in sterile water.

Purified PCR products (150 ng of each) were ligated to SfiI site of pAK200 vector overnight at 16° C. (molar ratio insert:vector=1:2).

Ligation of library to pAK200 vector was very efficient: by agarose gel electrophoresis and restriction analysis we found that 100% library scFv DNA was ligated at least to one side of the vector and more than 50% was connected to spacer part of the plasmid.

In order to introduce features necessary for polysome display ligation mixtures were amplified in two steps by PCR using in the first step oligonucleotides SDA (5'-AGACCACAACGGTTTCC-CTCTAGAAATAATTTT-GTTTAACTTTAAGAAGGAGATATATCCATGGACTA-CAA AGA-3') (SEQ ID NO: 14), which introduces a ribosome binding site (RBS), and ON7 (SEQ ID NO: 9) (see Example 1), which introduces a translated T3Te terminator, and in the second step oligonucleotides T7B (5'-ATAC-GAAATTAATACGACTCACTATAGGGAGACCACAA-CGG-3')(SEQ ID NO: 15), which introduces the T7 promoter and the 5'-loop, and oligonucleotide ON7 (SEQ ID NO: 9). PCR products were directly used for in vitro transcription without additional purification, and RNA was purified by LiCl precipitation (Pokrovskaya, I. D. & Gurevich, V. V. (1994) *Anal. Biochem.* 220, 420–423). RNAs from both mini-libraries were pooled in equal ratio and used for polysome display.

EXAMPLE 9

In vitro Translation of a Library of scFv Antibody Fragments

In vitro translation in an *E. coli* S-30 system was performed as described in Example 6 with small modifications. In short in vitro translation was carried out for 8 min at 37° C. in a 220 µl reaction which contained the following components: 50 mM Tris-Ac, pH 7.5, 30 mM NH4Ac, 12.3 mM Mg(Ac)$_2$, 0.35 mM of each amino acid, 2 mM ATP, 0.5 mM GTP, 1 mM cAMP, 0.5 mg/ml *E. coli* tRNA, 20 µg/ml folinic acid, 100 mM KAc, 30 mM acetylphosphate, 1.5% PEG 8000, 33 µg/ml rifampicin, 1 mg/ml vanadyl ribonucleoside complexes (VRC), 3.5 mM anti-ssrA oligonucleotide, 0.3 µM PDI, 51.4 µl of *E. coli* MRE600 extract and 90 µg/ml of mRNA.

EXAMPLE 10

Screening of scFv Library

Affinity Selection of Polysome Complexes and RNA Isolation

In a first approach, affinity selection was performed as described in Example 6 with the improvement of using heparin during selection. We observed that heparin decreases unspecific binding of polysome complexes to specific (GCN4(7P14P) (SEQ ID NO: 13)-BSA) as well as to unspecific surface (milk or BSA).

The translation (see Example 9) was stopped by adding Mg(Ac)$_2$ to a final concentration of 50 mM, and the translation mixture was cooled on ice. The samples were diluted four-fold with ice-cold washing buffer (50 mM Tris-Ac pH 7.5, 150 mM NaCl, 50 mM Mg(Ac)$_2$, 2.5 mg/ml heparin and 0.1% Tween-20) and centrifuged for 5 min at 4° C. at 10.000×g to remove insoluble components. Microtiter plates coated with GCN4(7P14P) (SEQ ID NO: 13)-BSA conjugate were prewashed with ice-cold washing buffer, and the supernatant from the centrifuged translation mixture was applied (200 μl per microtiter well) and the plate was gently shaken for 1 h in the cold room. After 5 washes with ice-cold washing buffer without heparin, the retained polysome complexes were dissociated with ice-cold elution buffer (100 μl per well; 50 mM Tris-Ac, pH 7.5, 150 mM NaCl, 10 mM EDTA, 50 μg/ml of E. coli tRNA) for 10 min in the cold room, and released mRNA was recovered by isolation using the RNeasy kit (Qiagen) and used for RT-PCR.

After in vitro transcription of PCR products, RNA was purified by LiCl precipitation (Pokrovskaya, I. D. & Gurevich, V. V. (1994) Anal. Biochem. 220, 420–423) and used either for RIA analysis (see below) or for the next round of polysome display.

To further improve affinity selection, the use of competing proteins during selection was evaluated. Using milk during affinity selection of polysome complexes to GCN4(7P14P) (SEQ ID NO: 13)-peptide resulted in no RNA isolated after a polysome display cycle probably due to milk's RNase activity. Pure proteins (e.g. BSA, casein or transferrin) did not decrease unspecific binding. Surprisingly, we observed that milk could be used during affinity selection of polysome complexes if it was sterilized. Thus, it had no influence on RNA stability and substantially decreased unspecific binding to the surface.

In this second approach, the conditions described above were used with the modification of having 2% sterilized milk in the buffer during affinity selection.

Radioimmunoassay (RIA)

After each round of polysome display, RNA of the whole recovered pool was in vitro translated in the S-30 E. coli system using similar conditions as described for the library above with the following modifications: translation was carried out for 30 min at 37° C., the reaction mixture contained 50 μCi/ml of 35S-methionine and 0.35 mM of each amino acid except methionine, and anti-ssrA oligonucleotide as well as PDI were absent. After translation, the reaction mixture was diluted four fold with PBST/milk to a final concentration of 2% milk and bound to immobilized GCN4(7P14P) (SEQ ID NO: 13) peptide in a microtiter well. After 30 min incubation with gentle shaking, microtiter wells were washed 5 times with PBST and bound radioactive protein was eluted with 0.1 M triethylamine. Eluted protein was quantified in a scintillation counter. Inhibition RIA was carried out by preincubation of the translation mixture diluted to PBST/2% milk with the GCN4(7P14P) (SEQ ID NO: 13) peptide at different concentrations at least 1 hour at room temperature prior to binding to immobilized antigen.

ELISA of Single Clones

After the 3rd round of polysome display PCR products were cloned into the vector pTFT74 (Ge, L., Knappik, A., Pack, P., Freund, C., & Plückthun, A. (1995) Antibody Engineering, ed. Borrebaeck, C. A. K. (Oxford University Press, New York)). Plasmids of single clones were isolated, transcribed in vitro (3), RNA was purified by LiCl precipitation (3) and used for in vitro translation in the S-30 E. coli system using similar conditions as described for the library above with the following modifications: translation was carried out for 30 min at 37° C., and anti-ssrA oligonucleotide, VRC as well as PDI were absent. After translation, the reaction mixture was diluted four fold with PBST/milk to a final concentration of 2% milk, with the mixture containing GCN4(7P14P) (SEQ ID NO: 13) peptide at different concentrations, and pre-incubated for 1 h at room temperature. Binding to immobilized GCN4(7P14P) (SEQ ID NO: 13) peptide in a microtiter well was carried out for 30 min with gentle shaking, and bound scFv protein was detected using the monoclonal anti myc-tag antibody 9E10 and a polyclonal anti-mouse/peroxidase conjugate (Pierce).

Results

Figure 5A:
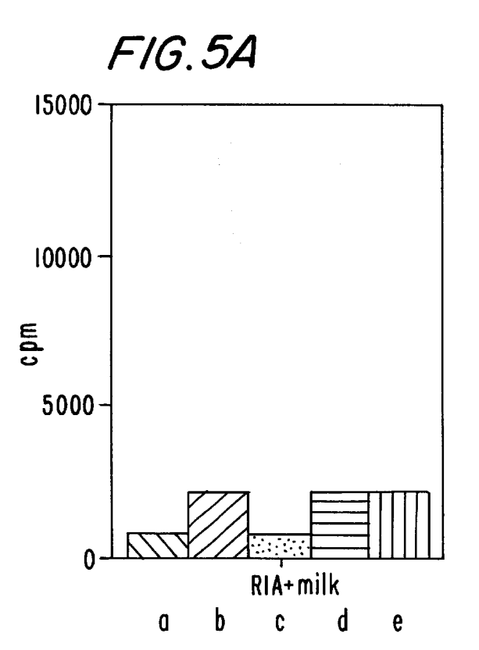
Figure 5B:
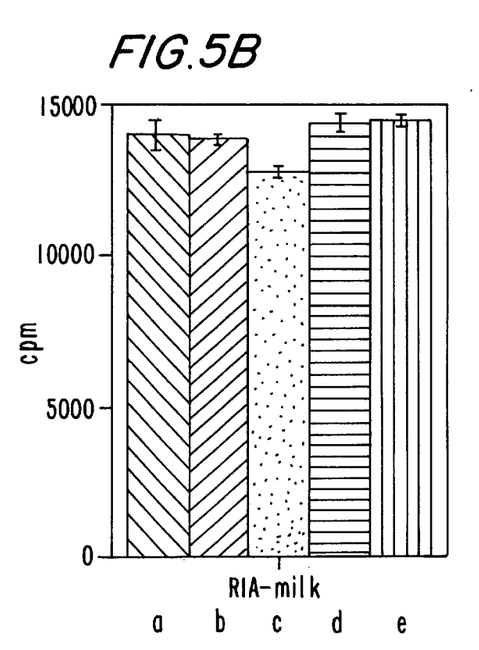

After the 3rd round of polysome display without addition of milk, we analysed the pool of binders by RIA (using 2% milk) for binding to the GCN4(7P14P) (SEQ ID NO: 13) peptide and found that the pool binds and can almost completely be inhibited by 1 μM peptide. No inhibition with hag peptide as well as with fluorescein was observed (FIG. 5A). However, analysis of single clones of the pool by ELISA (using 2% milk) revealed that among 24 clones only 3 bound the GCN4 (7P14P) (SEQ ID NO: 13) peptide and could be inhibited with it (positive clones). The other 21 clones did not bind the target peptide and were probably binding unspecifically to the surface. Further 2 polysome display rounds did not increase the RIA signal of the pool indicating that there was no further enrichment for binders. Because we did not use milk during affinity selection of polysome complexes and it is known from phage display experiments that milk decreases unspecific binding of phages to surfaces we repeated RIA of pools as well as ELISA of single clones in the absence of milk. RIA of the pool in the absence of a milk revealed that the pool contains unspecific binders as well (FIG. 5B). Analysis of single clones showed that binding properties of 3 positive clones were not influenced by the presence of 2% milk during ELISA, however, unspecific binders bound to the surface in the absence of milk but did not bind at all in the presence of 2% milk.

Figure 5C:
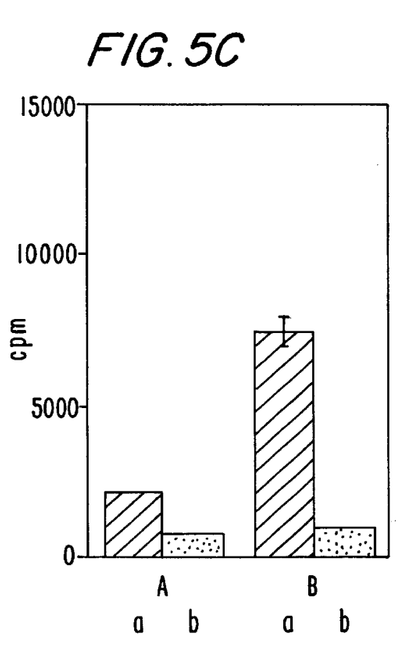

Affinity selection was repeated with addition of 2% milk. After the 3rd round we again analysed the pool by RIA for binding to the GCN4 (7P14P) (SEQ ID NO: 13) peptide. In that case the pool gave about 4 times more bound protein than the pool obtained without milk and was nearly completely inhibited by 1 μM peptide (FIG. 5C). Analysis of single clones out of this pool by ELISA revealed that approximately 75% of clones were positive.

TABLE 1

Mutations in scFvhag fragments selected by ribosome display in vitro.

| Clone No. | Mutation $V_L$ | Mutation $V_H$ | Mutation Linker | relative RIA signal | rel. RIA signal (+hag) | Inhibition (%) |
|---|---|---|---|---|---|---|
| 12 | K45R | P41R | | 102 | 6 | 94 |
| 10 | | S30P | | 101 | 5 | 95 |
| *6 | | | | 100 | 4 | 96 |
| *2 | | | | 96 | 5 | 95 |
| 7 | | G16D | | 89 | 5 | 95 |
| 3 | Y49H | | | 86 | 5 | 95 |
| 9 | E55G, E105G | A23V | S5P | 86 | 5 | 94 |
| 1 | T20A | | G12E | 80 | 3 | 96 |
| 18 | N(27d)D | D10G, T50N | | 76 | 5 | 93 |
| 4 | V13A, K28R | V12A | | 72 | 6 | 91 |
| 13 | V58I | Y79C | | 65 | 8 | 87 |
| 16 | L83R | I51V, K75E, A113V | | 63 | 5 | 92 |
| 14 | K30E | D61G | S5P | 43 | 6 | 85 |
| 17 | F71S | | | 18 | 6 | 66 |
| 8 | E17G, K18E, K30E | | | 14 | 6 | 56 |
| 5 | L11P | | G13D | 9 | 5 | 51 |
| 11 | S(27e)F, N90S | V48I | | 9 | 7 | 22 |
| 15 | G64D, S77A | G15S | | 6 | 6 | 2 |

Mutations in the scFv of the antibody 17/9 (Schulze-Gahmen, U., Rini, J. M. & Wilson, I. A. (1993) J. Mol. Biol.

234, 1098–1118) are numbered according to Kabat, E. A., Wu, T. T., Perry, H. M., Gottesmann, K. S. & Foeller, C. (1991) in *Sequences of Proteins of Immunological Interest*, vol. I. (US Department of Health and Human Services, 5th ed.), pp. 151 and 464, in the variable domains, and sequentially in the linker. Clones are sorted according to a relative RIA signal. Wild-type clones 2 and 6 are marked by an asterisk. RIAs were normalized to the same amount of full length protein and inhibited by 0.1 mM hag peptide (denoted as +hag), to verify binding specificity.

---

We claim:

1. A method for identifying a nucleic acid molecule encoding a peptide or polypeptide that interacts with a target molecule comprising the steps of:

(a) translating a population of mRNA molecules devoid of stop codons in the correct reading frame in an in vitro prokaryotic translation system under conditions that allow the formation of polysomes, wherein said translation system is free of ssrA-RNA, and wherein said population of mRNA molecules is protected from ribonuclease activity;

(b) bringing the polysomes so formed into contact with said target molecules under conditions that allow the interaction of the peptides or polypeptides encoded by said mRNA molecules and displayed by said polysomes with said target molecules;

(c) separating polysomes displaying peptides or polypeptides that interact with said target molecules from polysomes displaying no such peptides or polypeptides; and (d) identifying the nucleic acid molecule encoding a peptide or polypeptide displayed in a polysome that interacts with said target molecules.

2. A method according to claim 1, wherein the peptides or polypeptides encoded by said population of mRNA molecules comprise mutagenized polypeptides.

3. A method according to claim 1, wherein the peptides or polypeptides encoded by said population of mRNA molecules comprise a library of proteins or peptides.

4. A method for identifying a nucleic acid molecule encoding a peptide or polypeptide that interacts with a target molecule comprising the steps of:

(a) translating a population of mRNA molecules devoid of stop codons in the correct reading frame in an in vitro prokaryotic translation system under conditions that allow the formation of polysomes, wherein said translation system comprises antisense oligonucleotides complementary to the tag-coding sequence of ssrA-RNA, and wherein said population of mRNA molecules is protected from ribonuclease activity;

(b) bringing the polysomes so formed into contact with said target molecules under conditions that allow the interaction of the peptides or polypeptides encoded by said mRNA molecules arid displayed by said polysomes with said target molecules;

(c) separating polysomes displaying peptides or polypeptides that interact with said target molecules from polysomes displaying no such peptides or polypeptides; and (d) identifying the nucleic acid molecule encoding a peptide or polypeptide displayed in a polysome that interacts with said target molecules.

5. A method according to claim 4, wherein the peptides or polypeptides encoded by said population of mRNA molecules comprise mutagenized polypeptides.

6. A method according to claim 4, wherein the peptides or polypeptides encoded by said population of mRNA molecules comprise a library of proteins or peptides.

7. A method for identifying a nucleic acid molecule encoding a peptide or polypeptide that interacts with a target molecule comprising the steps of:

(a) transcribing a population of DNA molecules devoid of stop codons in the correct reading frame into the corresponding population of mRNA molecules in the presence of a reducing agent;

(b) removing said reducing agent from said population of mRNA molecules;

(c) translating said population of mRNA molecules in an in vitro prokaryotic translation system under conditions that allow the formation of polysomes, said translation system lacking functional ssrA-RNA;

(d) bringing the polysomes so formed into contact with target molecules under conditions that allow the interaction of peptides or polypeptides encoded by said mRNA molecules and displayed by said polysomes with said target molecules;

(e) separating polysomes displaying peptides or polypeptides that interact with said target molecules from polysomes displaying no such peptides or polypeptides; and (f) identifying the nucleic acid molecule encoding a polypeptide or peptide displayed in a polysome that interacts with said target molecules.

8. A method according to claim 7, wherein the peptides or polypeptides encoded by said population of mRNA molecules comprise mutagenized polypeptides.

9. A method according to claim 7, wherein the peptides or polypeptides encoded by said population of mRNA molecules comprise a library of proteins or peptides.

* * * * *